United States Patent [19]

Wertz et al.

[11] Patent Number: 4,986,839
[45] Date of Patent: Jan. 22, 1991

[54] SELF-CONTAINED AIR ENHANCEMENT AND LASER PLUME EVACUATION SYSTEM

[75] Inventors: Thomas J. Wertz, The Woodlands; Russell W. Todd; Gerald D. Abell, both of Spring, all of Tex.

[73] Assignee: Surgical Laser Products, Inc., The Woodlands, Tex.

[21] Appl. No.: 269,629

[22] Filed: Nov. 10, 1988

[51] Int. Cl.[5] ............................................. B01D 19/00
[52] U.S. Cl. ..................................... 55/274; 55/316; 55/387; 55/467; 55/524; 55/498
[58] Field of Search ................. 55/316, 274, 387, 467, 55/471–473, 498, 524

[56] References Cited

U.S. PATENT DOCUMENTS

| | | | |
|---|---|---|---|
| 1,789,262 | 1/1931 | Monro et al. | 183/47 |
| 2,505,173 | 4/1950 | Conley | 128/141 |
| 3,012,322 | 12/1961 | Thompson | 32/33 |
| 3,308,609 | 3/1967 | McCulloch et al. | 55/472 |
| 3,680,560 | 8/1972 | Pannier, Jr. et al. | 128/276 |
| 3,843,865 | 10/1974 | Nath | 219/121 L |
| 3,889,657 | 6/1975 | Baumgarten | 128/2 B |
| 3,910,276 | 10/1975 | Polanyi et al. | 128/303.1 |
| 3,982,541 | 9/1976 | L'Esperance, Jr. | 128/303.1 |
| 4,143,660 | 3/1979 | Malyshev et al. | 128/303.1 |
| 4,182,385 | 1/1980 | Williamson | 141/65 |
| 4,266,549 | 5/1981 | Kimura | 128/303.1 |
| 4,487,606 | 12/1984 | Leviton et al. | 604/319 |
| 4,496,378 | 1/1985 | Kish | 55/316 |
| 4,516,973 | 5/1985 | Telang | 604/319 |
| 4,619,672 | 10/1986 | Robertson | 55/316 |
| 4,810,269 | 3/1989 | Stackhouse et al. | 55/319 |
| 4,826,513 | 5/1989 | Stackhouse et al. | 55/316 |

FOREIGN PATENT DOCUMENTS

3309497  9/1984  Fed. Rep. of Germany ........ 55/387

OTHER PUBLICATIONS

Jan-L Company, "150 L Office Model Laser Smoke/Odor Extractor", Mt. Holly, N.J.
Stackhouse Associates, "The Stackhouse System", El Segundo, Calif.
Mihashi et al., "Some Problems About Condensates (Smoke) Induced by Carbon Dioxide Laser Irradiation", Surgimedics, Sugar Land, Tex.
Lotze, "Safety Considerations & Clinical Points Relating to Proper Application of Laser Energy", Woman's Hospital of Texas.
Lase, Inc., "The LASE System", Cincinnati, Ohio.
Lase, Inc., "The LASE System II", Cincinnati, Ohio.
Lase, Inc., "The LASE Evacuator/Aspirator", Cincinnati, Ohio (1988).
Custom Laser Accessories & Suction Systems, Inc., "Laser Fume/Smoke Evacuator", Richardson, Tex.
XIMED Medical Systems, "X-Smoke TM Laser Smoke Evacuator & Disposable Filters", Santa Clara, Calif. 95050 (publication date currently unknown).
Lase, Inc., "The LASE System II", Cincinnati, Ohio (publication date currently unknown).

*Primary Examiner*—Bernard Nozick
*Attorney, Agent, or Firm*—Workman, Nydegger & Jensen

[57] ABSTRACT

A system for filtering the harmful particulates and liquids from a laser plume formed during surgical procedures. The laser plume may be passed through a suction canister to remove a liquid component from the laser plume. Thereafter, the laser plume is passed through a filter containing granular activated charcoal and a pleated filter to remove substantially all toxic elements and particulate matter in the laser plume. The system is self-contained and is configured such that the air from the laser plume is not cross-contaminated with either the ambient air in the room or the cooling air of the vacuum motor. The system also contains a pressure differential measuring device for indicating to the medical personnel when the filter of the present invention needs to be changed. Because of the unique configuration of the present invention, it is capable of running at increased suction levels while running at reduced noise levels as compared with conventional systems of this nature.

16 Claims, 5 Drawing Sheets

SELF-CONTAINED AIR ENHANCEMENT AND LASER PLUME EVACUATION SYSTEM

BACKGROUND

1. The Field of the Invention

This invention relates to a system for enhancing the air within the surgical site during laser surgery. More particularly, the present invention is directed to a self-contained air enhancement system for evacuating the smoke plume created by use of the laser.

2. The Prior Art

The use of lasers in surgery has rapidly expanded in recent years. Initially, lasers were found to be particularly useful in very delicate surgery and surgery which requires extreme precision. As a result, the use of lasers in eye surgery and other types of microsurgery became well accepted during the 1970's. Indeed, many laser surgical devices incorporated a microscope into a laser source so that the area on which surgery was performed could be adequately and accurately viewed.

Since this early introduction of lasers into surgical procedures, they have found acceptance in more general areas of surgery outside of the microsurgical area. For example, lasers have currently found wide acceptance in the area of gynecological surgery.

With the rapid expansion in the use of lasers as surgical instruments, new problems have been encountered which are not generally encountered in conventional surgery. One serious problem is that of smoke produced during laser surgery. This smoke produced during laser surgery is generally referred to as a "laser plume."

Because of the high intensity of lasers used in laser surgery, tissue contacted by the laser may be rapidly and almost competely oxidized. The oxidized tissue typically results in a dense plume emitted from the surgical area. While the plume, consisting of oxidized tissue, is generally free of viable organic material, it has been found that the plume contains a variety of hydrocarbon compounds and carbon monoxide. While some smoke may be produced by conventional electric scalpels and similar devices, the intensity and volume of the smoke and pollutants produced in laser surgery presents a problem of much larger magnitude.

In one study which sought to determine the scope and intensity of the smoke produced during surgery, tissue was contacted by a laser under controlled conditions. It was found that the smoke and particulate matter produced amounted to almost 7.9 milligrams per cubic meter. This smoke density is approximately 52 times greater than the recommended density set by the governmental regulatory agencies.

In addition, the laser plume is known to contain particles of varying sizes. For example, one investigation found particles varying in size from under 0.4 microns to over 9.0 microns. Nevertheless, a large portion of the particles found in that study were under 1.1 microns in size; particles of this size are capable of being easily deposited in the alveoli of the lungs. Not only are particles of this size irritating to the respiratory system, but they may also be capable of causing serious respiratory disease. Moreover, repeated exposure to such particles can build within the lungs.

Several investigators have pointed out that repeated exposure to laser plumes may, for example, result in pneumonitis. In addition, it has been found that the laser plume is potentially mutagenic, and thus possibly carcinogenic. While much of the data in this area is still not definitive, it is clear that direct contact with laser plumes presents significant health risks, particularly to the medical personnel who are repeatedly exposed to such laser plumes.

Apart from the very significant problems resulting from inhaling the laser plume, laser plumes present additional difficulties. For example, it has been found that the laser plume may condense on the optical components of the laser itself, thereby causing pitting damage of the lenses. Similarly, the laser plume may enter mechanical devices and filters located in the operating room and clog or damage those devices and filters.

In order to combat the problems of damage to the laser itself by the laser plume, many modern conventional laser systems are equipped with air circulation systems. Typically, these systems drive a stream of air over the sensitive laser equipment and out toward the area being contacted by the laser beam. Thus, the laser plume is driven away from the laser equipment. However, it is found that this air flow forces the plume into the ambient air, thereby making it more difficult to control laser plume emissions.

Also of significance is the fact that the superheated steam component of the laser plume may cause serious burns in the event it comes into contact with the flesh. Of course, the primary danger in this regard is to the patient. Since the steam is produced by vaporizing body fluids, it is clear that there is a danger that those vaporized fluids may contact the surrounding tissue.

Nevertheless, in the event the steam leaves the localized surgical site, there is a danger that the heat associated with the steam may cause discomfort or otherwise provide an undesirable distraction to the surgeon or other operating room personnel. Thus, it is important that the steam produced in laser surgery be controlled and removed from the surgical site before exposure to the tissues surrounding the surgical site to operating room personnel.

Because of the potential harm caused by the laser plume, good practice dictates that the laser plume be controlled and removed from the surgical site before it contacts the patient, the laser equipment, or enters the ambient air. Thus, various devices have been developed for removing the laser plume; most of these devices involve the use of suction in some form.

The initial attempt to remove the laser plume was to simply use the operating room's built-in vacuum system to provide suction for removal of the plume. This solution, however, was found to be totally unsatisfactory because the building's vacuum system is not equipped to handle the dense hydrocarbon saturated smoke and associated particulates contained within the laser plume. The untreated laser plume has been found to clog and completely disable the entire hospital's vacuum system—a completely unacceptable result.

Because laser surgery often requires intense concentration on the part of the surgeon, as well as many other medical personnel, it is desirable to keep machinery and distractive noise in the operating room to a minimum. A significant disadvantage of the use of a portable vacuum system is the undesirable noise created in the operating room. Additionally, such a system can have significant resistance to air flow because of filters which easily become clogged with the particulate debris and other matter contained within the laser plume which is suctioned from the operating site. Unfortunately, a portable system has a limited filter capacity which renders their use ineffective because laser surgery creates greater wastes than result from more traditional surgical procedures.

This resistance to air flow significantly limits the flow rate of air traveling through the system, causing the laser plume removal process to be less efficient. Because the filters of conventional systems become clogged easily, they must be replaced more often to ensure that suction levels are adequate for removing the laser plume from the surgical site. This results in increased maintenance and cost, as well as possible disruption to the surgical procedure.

Studies have been performed concerning various methods for removing laser plumes. It has been found that if a suction device having appropriate air flow rates can be placed within approximately 1 centimeter of the source of the laser plume, then over 98% of the smoke and debris will be removed before it enters the ambient air. However, if the suction source with the same air flow is placed 2 centimeters from the source, only slightly over 50% of the smoke in the plume is removed. Thus, it will be appreciated that in the setting of the surgical theatre, it is important that laser plume removal systems be flexible and maneuverable, not bulky and hard to handle.

In view of the problems encountered in removing the laser plume from a surgical site, it would be a significant advancement in the art if a device could be provided which avoided the problems in the prior art identified above. Specifically, it would be an advancement in the art if a laser plume aspiration system could be provided which was inexpensive, easy to handle and flexible in use.

It would be a further advancement if such a system were compact, self-contained, and quiet in operation. It would also be a very significant advancement in the art if such a system could maintain a higher flow rate of air than conventional systems without the usual increased maintenance of having to change the filter more frequently. Such a device and aspiration system are disclosed and claimed herein.

BRIEF SUMMARY AND OBJECTS OF THE INVENTION

The current invention is directed to a compact, self-contained laser plume evacuation system and filter for use in laser surgery. One important feature of the current invention is its advanced design which permits greater flow rates of air through the system while avoiding the increased maintenance and other disadvantages which typically accompany increased flow rates in conventional systems.

While several different embodiments of the current invention are disclosed herein, currently preferred embodiments of the invention comprise a system housing with an inlet tube having an inside diameter of 1.25 inches to 1.345 inches, which are much larger than the inlet tubes on conventional systems. The inlet tube is configured with a smooth inner wall. This smooth-wall configuration keeps to a minimum the turbulence in the air flowing through the tube.

Because the noise generated by the air flow through the tube is largely a function of the turbulence of the air flow, noise levels are decreased by employing the smooth-wall tubing. On its free end, the inlet tube is configured with a connector (preferably rigid and transparent) which enables the tube to be connected to a conventional suction wand or aspirator which provides suction at the surgical site.

The laser plume is drawn into the system through the inlet tube. For closed surgical procedures, the inlet tube directs the laser plume through a suction canister where any liquid aspirated from the surgical site with the laser plume is removed. "Closed procedures" refers to those surgical procedures which require no incision, or only a small incision, in the patient. For example, this may include internal examination of a patient with an endoscope, such as a laparoscope. The suction canister is mounted on the side of the system to facilitate its use, when needed.

For open surgical procedures, i.e., when the surgical site is exposed, the suction canister is not used. Thus, the inlet tube is attached directly to the system, as is explained in further detail below.

In one embodiment of the present invention, the inlet tube is attached directly to a reusable prefilter housing. Discs containing ultrafine charcoal may be located within the prefilter housing. The prefilter removes a portion of the toxic elements contained within the laser plume.

The prefilter housing is attached to a primary filter contained within the system housing such that after the laser plume has passed through the prefilter, it is forced through the primary filter. The primary filter includes a section of granular activated charcoal which reacts with the gases in the laser plume to remove their toxic elements. The primary filter also contains a void space through which the air obtains an evenness of flow to reduce the turbulence of the air as it passes through the primary filter. Finally, the primary filter contains a pleated safety filter designed to eliminate virtually all particles not trapped previously in the filtering system. After the air from the laser plume has passed through the primary filter, the filtered air is allowed to escape into the ambient air through an exhaust chamber.

In an alternative embodiment of the present invention, the inlet tube is attached to a single-use, prefilter. The prefilter is used in combination with a vacuum-formed disposable cap which is permanently bonded to the top of the filter. This prefilter may also contain ultrafine charcoal impregnated discs which provide additional vapor removal efficiency over those units described in the prior art. After flowing through the prefilter, the laser plume is directed into the primary filter.

In this embodiment of the present invention, the primary filter contains a segment of granular activated charcoal which removes the toxic gaseous products from the laser plume. A vertically pleated filter is provided within the base of the filter and is configured in a cylindrical shape such that the surface area of filter exposed to the flow of air through the filter is substantially increased over that of the previously described embodiment. The vertically pleated filter removes virtually all particulate debris not previously removed from the laser plume.

Other embodiments of the present invention may utilize variations of the primary filter described above. For example, rather that contain a segment of charcoal along a portion of the length of the primary filter, the primary filter may be filled completely with granular activated charcoal which surrounds the vertically pleated filter. Alternatively, a single-use in-line filter may be employed which is configured according to either of the embodiments described above.

A motor for generating suction is also provided within the system housing. This vacuum provides the suction force by which the laser plume is forced through the system. The system also includes within the system housing, a device for measuring the static pressure differential between the intake flow of air and the outlet flow of air, whereby the resistance to the passage of air through the filter may be measured. Thus, to determine whether the pressure differential has reached a certain predetermined level, the unit may be placed in "test" mode and an indicator light will be actuated to inform the operator or other medical personnel that the filter should be replaced.

A venting system for providing cooling air for the vacuum motor is also provided. The cooling air which circulates through this venting system is preferably maintained entirely separate and independent from the air filtered from the laser plume. This ensures that air which has been aspirated from the surgical site and filtered is not contaminated with ambient air which may contain particulate matter or toxic elements.

It will be appreciated that the current invention is simple and easy to use. Because of its efficient design, the present invention provides better filtration than systems taught in the prior art while having the capability to provide greater suction capabilities at reduced noise levels.

It is, therefore, a primary object of the present invention to provide an effective and efficient system for removal of the laser plume from the site of laser surgery.

It is an additional object of the present invention to provide self-contained means for aspirating a laser plume and filtering the laser plume to provide clean, non-toxic air.

It is still another object of the present invention to provide a laser plume evacuation system which is simple to operate and employs filters which are inexpensive to manufacture and which are capable of being produced in either a disposable form or a reuseable form.

It still another object of the present invention to provide a laser plume evacuation system which is capable of increased air flow rates while maintaining noise levels below those found in prior art systems.

It is a further object of the present invention to provide a laser plume evacuation system which uses inexpensive, but effective, filters and which is configured so that the filters may be easily and conveniently replaced.

It is another object of the present invention to provide a laser plume evacuation system which is self-contained and does not rely on a hospital vacuum system, thereby eliminating the risk that the hospital vacuum system does not provide sufficient suction for the needs of the laser surgeon.

These and other objects of the invention will be apparent upon reading the following detailed description and appended claims, with reference to the accompanying drawings.

DETAILED DESCRIPTION OF THE PREFERRED EMBODIMENTS

Figure 1:
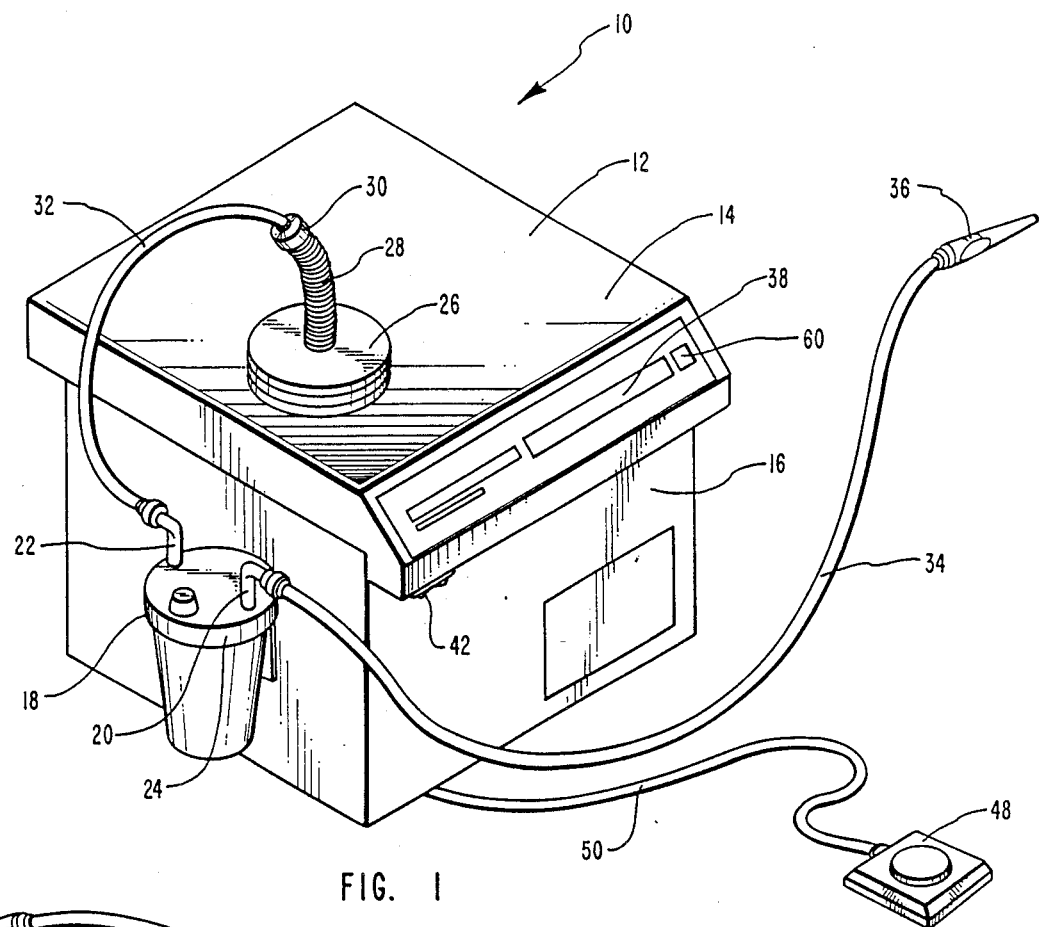
FIG. 1 and 1A are perspective views of the self-contained laser plume evacuation system of the present invention.
Figure 1A:
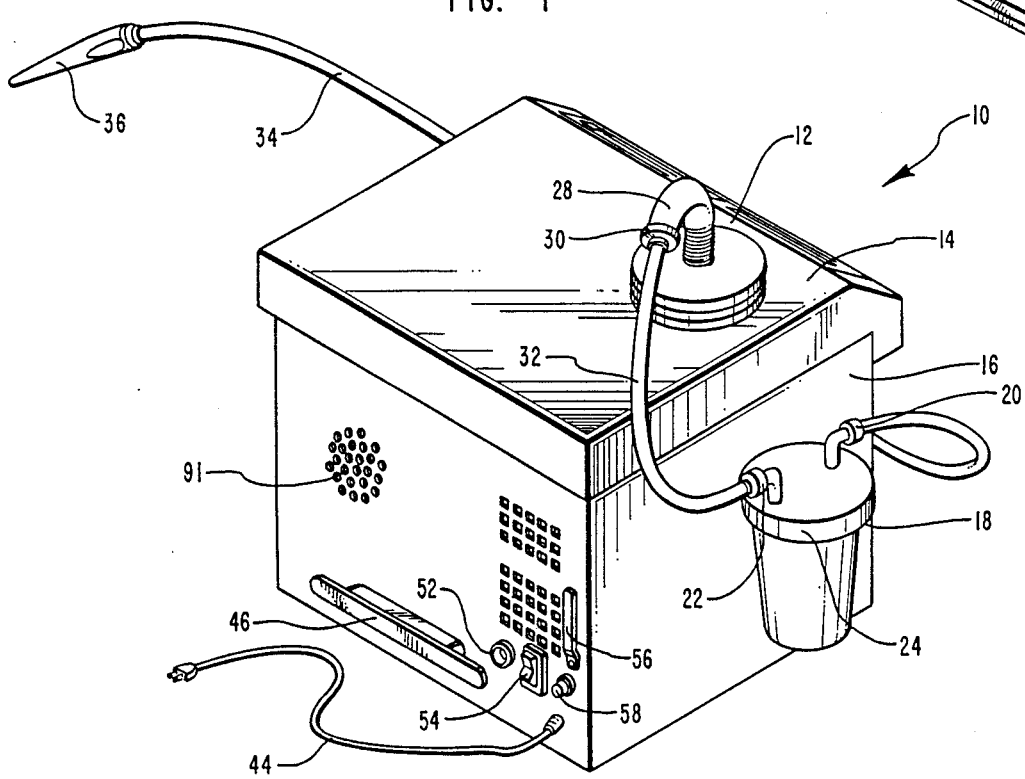

The present invention can best be understood by reference to the drawings, wherein like parts are designated with like numerals throughout. Referring now to FIGS. 1 and 1A, the laser plume evacuation system of the present invention is generally designated 10. A system housing 12 is provided in which the various components of the system are housed. System housing 12 comprises a system top housing 14 and a system bottom housing 16. System housing 12 may be made out of a variety of materials. It is presently preferred that the material have a smooth finish to facilitate its cleaning by medical personnel.

A suction canister 18 is provided which, as will be described in greater detail below, removes any liquids and gross particulate matter which are aspirated from the surgical site when the present invention is used for closed surgical procedures. The suction canister has an inlet port 20 and an outlet port 22 extending from it. Inlet port 20 is preferably configured to receive a ¼ inch conventional suction tubing.

Outlet port 22 is configured to receive a larger tubing, such as a ⅜ inch tubing, thereby providing greater suction capabilities at the surgical site without requiring the use of a larger motor. The suction canister is mounted to the side of the system housing by a mounting ring 24.

Still referring to FIGS. 1 and 1A, a prefilter housing top 26 is provided and configured to receive an inlet tube 28. It is presently preferred that inlet tube 28 have a large inside diameter, thereby providing for increased suction capabilities at the surgical site. In preferred embodiments of the present invention, inlet tube 28 has an inside diameter of 1.25 inches to 1.345 inches. A tube reducer 30 may be connected to the inlet tube to enable the inlet tube to be connected to a smaller diameter tube leading either to the surgical site or to the suction canister.

All of the suction tubes employed in the present invention are preferably transparent, thereby allowing the medical personnel to readily observe whether debris is accumulating at any point in the tubes. The tubes are constructed of any of the plastic compositions conventionally known in the plastics art for similar medical applications. The tubes are configured with a smooth inside surface thereby reducing any possibility that debris will build up, obstructing the flow of air through the system. Additionally, the smooth inside surface of the tubes helps reduce the noise which accompanies the flow of air through the tubes.

In the embodiment of the present invention illustrated in FIGS. 1 and 1A, a suction tube 32 is connected at one end to inlet port 20 of prefilter housing 26 via tube reducer 30 and at its distal end to outlet port 22 of suction canister 18. The inside diameter of suction tube 32, as illustrated in FIG. 1, is approximately ⅜ inch. A suction wand leader tube 34 is connected to inlet port 20 of suction canister 18 at one end and connected to a suction wand 36 at its opposite end. The suction wand is used to aspirate the laser plume from the surgical site.

In an alternative embodiment of the present invention, suction canister 18 is eliminated or bypassed and suction tube 32 is connected directly to the suction wand. In such an embodiment, it is preferable that a long length of inlet tube 28 (with a 1.25 inch to 1.345 diameter) be used which is connected to a short length of suction tube 32 by means of a suitable tube reducer. By maximizing the length of large-diameter tubing, the resistance in the system is minimized.

Suction wand leader tube 34 and suction wand 36 are provided in a sterile form for open surgical procedures, thereby maintaining sterile conditions at the surgical site.

By reducing the amount of smaller diameter tubing in the system, the suction capabilities of the system are increased without the necessity of providing a larger vacuum motor. An additional advantage of this configuration is that the increased noise levels associated with larger vacuum systems are eliminated. Noise levels are also kept to a minimum by employing suction tubes having a smooth inner surface, as explained above.

A suction control panel 38 is provided in the system top housing 14 so that the controller or other medical personnel can control the amount of suction at the surgical site. In one presently preferred embodiment of the present invention, the suction control panel contains ten different settings which may be used to obtain air flow rates from approximately 10 cubic feet per minute to approximately 50 cubic feet per minute. It will be appreciated that the control panel may be replaced with a dial or any other suitable means for adjusting the flow of air through the system.

A power switch 42 is mounted on the system top housing whereby the medical personnel can provide power to the system. Power is supplied to the system through power cord 44, which may be stored on the system housing by wrapping it around cord wrap bracket 46.

Alternatively, a foot switch 48 may be employed to facilitate turning on the system. Foot switch 48 includes foot switch cord 50 which enters system bottom housing 16 at foot switch port 52, as viewed in FIG. 1A. The operator of the system may control whether power switch 42 or foot switch 48 actuate power to the system with bypass switch 54.

Also mounted on system housing 12 is a tube holder bracket 56 through which excess tubing, such as suction wand leader tube 34, may be placed. A circuit breaker 58, such as those commonly employed in the electrical arts, may also be mounted on system housing 12.

To enable the operator of the system to test the system prior to using the system at the surgical site, a test button 60 is provided. Test button 60 is preferably mounted adjacent suction control panel 38 and may be actuated to indicate to the operator of the system whether the filter employed in the system needs to be changed, as will be explained below in further detail.

Because of the relative compact size of the system, the system may be mounted on a typical cabinet having drawers in which may be kept accessories to the system. Advantageously, the cabinet may have casters mounted at its base to render the system portable, thereby facilitating transportation of the system into the operating room.

Figure 2:
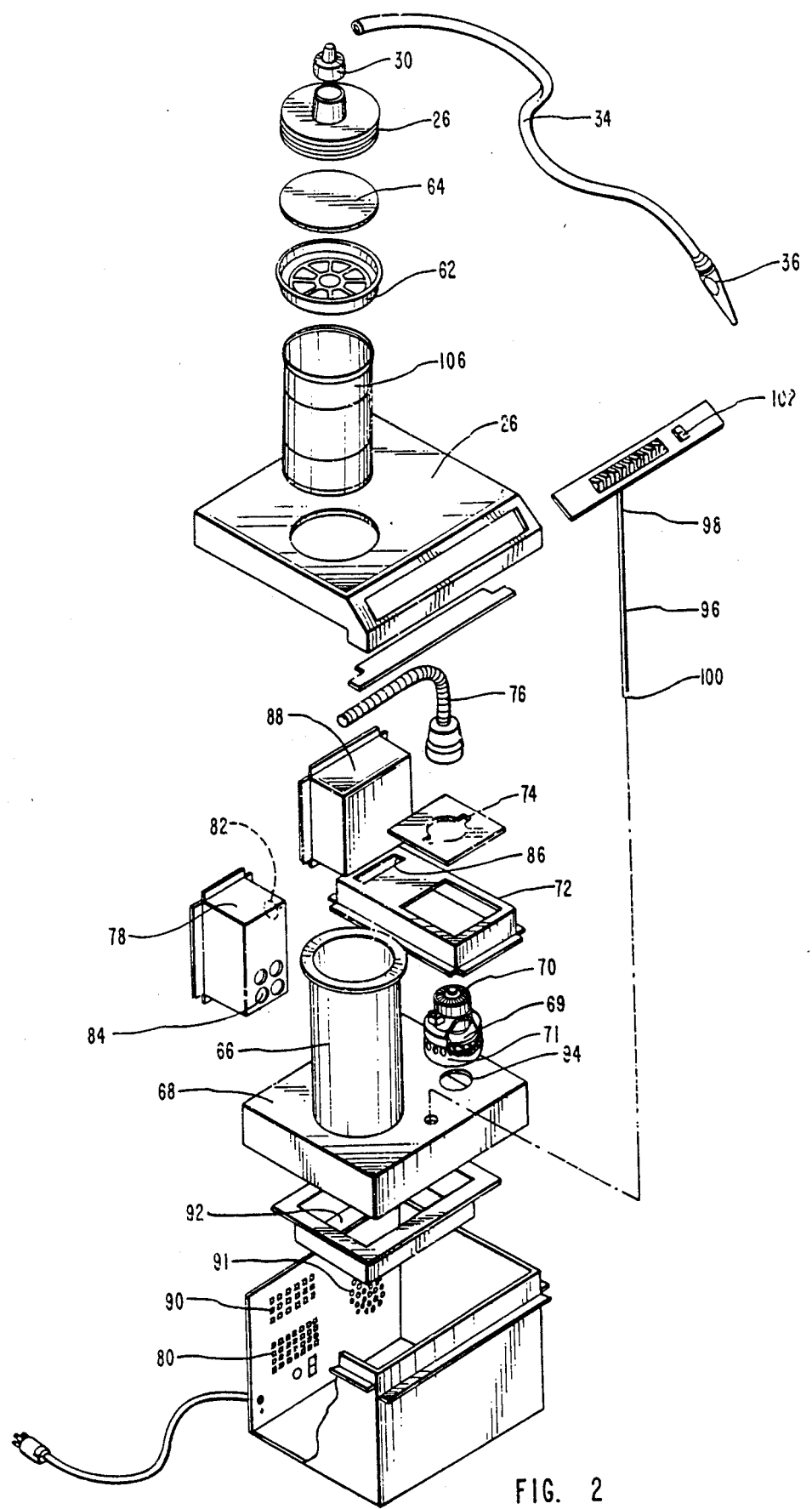
FIG. 2 is an exploded perspective view of the present invention.

Referring now to FIG. 2, the various components contained within the system housing 12 are illustrated and explained. Prefilter housing top 26 is connected directly to a prefilter housing base 62. Between prefilter housing top 26 and prefilter housing base 62 is placed a filter disc 64, which initially removes larger particulate matter from the laser plume. The prefilter housing base attaches to a filter canister 106 which may be placed into filter cylinder 66. Filter cylinder 66 is mounted to a base plate 68 within the system housing.

Also mounted to base plate 68 is a conventional means for creating suction, comprising by way of example, a fan 69 driven by a vacuum motor 70 and mounted in a fan housing 71. A vacuum motor retainer housing 72 is specially configured to fit over vacuum motor 70 and to be mounted to base plate 68. The vacuum motor retainer housing contains a keyed plate 74 which fits over the vacuum motor such that the motor component of the means for creating suction extends above housing 72.

A cooling air supply tube 76 channels ambient air for cooling vacuum motor 70. The cooling air for vacuum motor 70 is obtained through a cooling air supply/exhaust chamber 78. It is through the cooling air supply/exhaust chamber that cool, ambient air is provided through cooling air supply tube 76 to the vacuum motor.

The cooling air supply/exhaust chamber is open to the ambient air through a cooling air vent 90 contained in the side wall of system bottom housing 16. Cooling air supply/exhaust chamber 78 is configured with an inlet duct 82 through which ambient air flows into cooling air supply tube 76 and to the vacuum motor. After the cooling air has passed over the vacuum motor and provided its cooling function, it enters cooling air supply/exhaust chamber 78 through an exhaust duct 584 where it exits into the ambient air through cooling air vent 80.

Still referring to FIG. 2, vacuum motor retainer housing 72 is also provided with a filtered air duct 86 through which filtered air may flow into a filtered air exhaust chamber 88 and exit into the ambient air through a filtered air exhaust vent 91 contained in system bottom housing 16, as will be explained below in greater detail.

The flow of aspirated air through the system may be explained with reference to FIGS. 1 and 2. The laser plume is aspirated from the surgical site through suction wand 36. For closed procedures, the smoke and debris of the laser plume are directed into suction canister 18, as illustrated in FIG. 1, where the liquids and gross particulate matter contained within the laser plume are removed. Referring now to FIG. 2, the laser plume is then directed to prefilter housing top 26 through inlet tube 28. After flowing through the prefilter, the air passes through the primary filter, located within filter cylinder 66, where the toxic elements are removed from the air, as well as any particulate matter which may have not been removed by the prefilter.

In one aspect of the present invention, a self-contained air enhancement system as described above is provided with a means for shielding the laser plume from cross-contamination of ambient air used to cool vacuum motor 70. As shown by way of example in FIG. 2 and not limitation, the laser plume passes from primary filter cylinder 66 directly into a vacuum chamber 92. The vacuum motor is in direct connection with vacuum chamber 92 through an orifice 94 in base plate 68. Thus, as the vacuum motor is actuated, the resulting suction through orifice 94 causes reduced pressure in vacuum chamber 92 relative to the ambient pressure. The air which has now passed through the primary filter exits the vacuum chamber through orifice 94 where it passes through the vacuum motor and exits vacuum motor retainer housing 72 through filtered air duct 86. The filtered air duct is in direct connection with a filtered air exhaust chamber 88. Thus, as the filtered air exits the system, it flows through filtered air duct 86, into filtered air exhaust chamber 88, and is expelled into the ambient air through a filtered air exhaust vent 91 contained in the side of system bottom housing 16. The laser plume evacuation system of the present invention is thus configured such that the air provided to cool the vacuum motor is never mixed with the air being filtered through the system.

As air is filtered through the system, the primary filter becomes filled with particulate debris which causes the filter's resistance to the flow of air passing through the system to increase. To enable medical personnel to properly determine when the primary filter needs to be changed, a pressure differential tubing 96 and pressure differential switch are provided in the system which measure the pressure differential between the vacuum created in vacuum chamber 92 and the ambient air pressure. This feature may be accessed by placing the system in test mode by actuating test button 60.

As can be observed by reference to FIG. 2, pressure differential tubing 96 is mounted at its upper end 98, as viewed in FIG. 2, to the pressure differential switch on the inside of suction control panel 38 where it is exposed to ambient air pressure. The bottom end 100 of pressure differential tubing 96 is mounted to base plate 68 and is exposed to vacuum chamber 92. As the primary filter begins to be clogged with debris and the resistance to the passage of air through the filter increases, the pressure differential between the ambient air and the pressure within vacuum chamber 92 also increases.

In one presently preferred embodiment of the present invention, it has been found that the pressure differential between vacuum chamber 92 and the ambient pressure is approximately 10 inches of water when employing a clean filter in the system. It has also been found that it is desirable to replace the filter when the pressure differential, as measured by pressure differential tubing 96, reaches approximately 15 inches of water. The unit may be placed in "test" mode by actuating test button 60 which will illuminate an indicator light 102 when the pressure differential reaches a predetermined level. Thus, the medical personnel operating the system may test the system to properly determine when the primary filter needs to be replaced.

Figure 3:
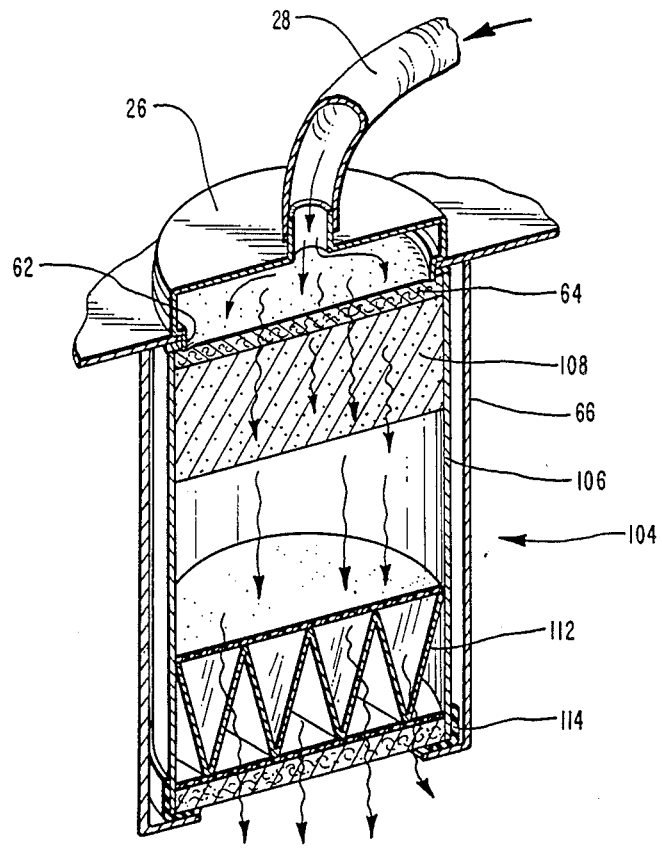
FIG. 3 is a cross-sectional perspective view of one embodiment of the filter employed according to the present invention.

One presently preferred embodiment of a primary filter of the present invention is illustrated in FIG. 3 and generally designated at 104. Inlet tube 28 is connected directly to prefilter housing top 26. In the embodiment of the present invention illustrated in FIG. 3, prefilter housing top 26 may be repeatedly used if cleaned after each use.

The prefilter housing top is preferably connected to a prefilter housing base 62 with a filter disk 64 inserted between the prefilter housing top and the prefilter housing base. Filter disk 64 may contain ultrafine charcoal to increase the vapor removal efficiency of the primary filter. Prefilter housing base 62 is attached to filter canister 106; the connection must be air tight such that no ambient air is allowed to enter the system at the connection in order to maintain maximum suction in the system.

The upper portion of filter canister 106 contains granular activated charcoal 108 which reacts with the laser plume to remove its toxic elements. After the laser plume flows through charcoal 108, it passes through an air flow stabilization chamber 110. The air flow stabilization chamber aids in providing evenness of air flow through the filter and in reducing the amount of turbulence in the air. The length of air flow stabilization chamber 110 is altered to adjust the height of filter canister 106.

Finally, the laser plume is directed through a pleated filter 112 located in the lower portion of filter canister 106 which removes any remaining particulate debris contained in the air. Filter canister 106 is sealed around its bottom edge 114 to prevent ambient air from entering the system.

Figure 4:
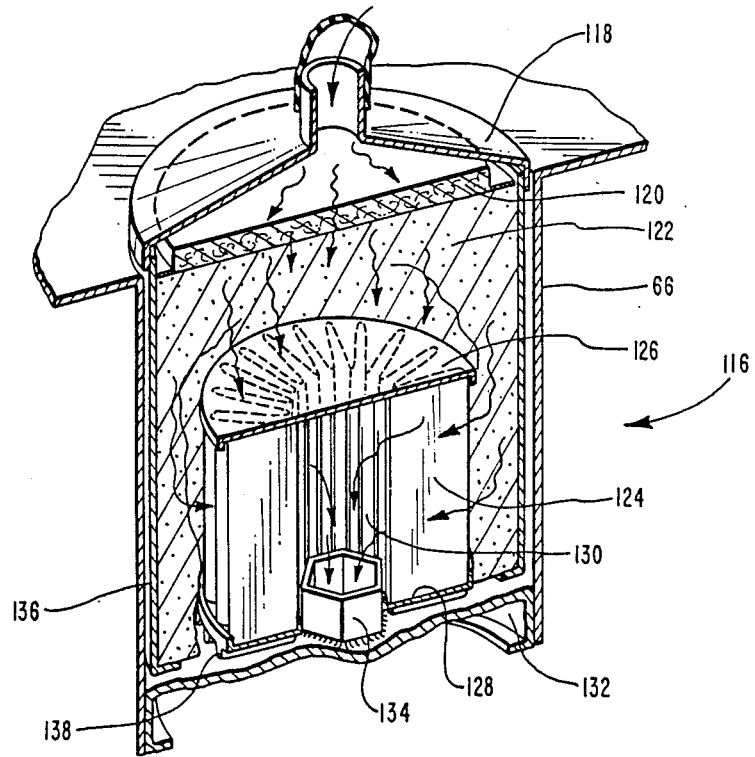
FIG. 4 is a cross-sectional perspective view of an alternative embodiment of the filter employed according to the present invention.

An alternative embodiment of the primary filter is illustrated in FIG. 4. In FIG. 4, the primary filter is generally designated 116. Primary filter 116 is provided with a prefilter housing 118 which, in this embodiment of the present invention, is a vacuum-formed disposable cap which is permanently bonded to filter canister 106.

As with the primary filter illustrated in FIG. 3, prefilter housing 118 of FIG. 4 also contains ultrafine charcoal impregnated disks 120 to assist in the filtering process. Prefilter housing 118 is attached directly to the filter canister and granular activated charcoal 122 is employed within filter canister 106 to detoxify the laser plume as it passes through primary filter 116.

A vertically pleated filter 124 having a cylindrical shape is preferably utilized within filter canister 106. Vertically pleated filter is made of glass fiber which facilitates the removal of very fine particulate matter. Because of the cylindrical geometry of the vertically pleated filter, substantially more filter surface area is exposed to the air traveling through the filter. This increases the filter efficiency and increases the life of the filter.

The vertically pleated filter is sealed at its top with a cap 126, preferably made out of metal. At its base, the vertically pleated filter is sealed to filter canister 106 by a potting material 128, such as urethane. This ensures that all air passing through filter canister 106 will flow through, rather than around, the vertically pleated filter.

As the air exits the filter canister, it flows through a filter exhaust tunnel 130. The shape of filter exhaust tunnel 130 may be of a variety of geometric configurations such as the hexagonal shape illustrated in FIG. 4. A tunnel adaptor 132 is provided in the base of filter cylinder 66 to adapt this filter, having a filter exhaust tunnel 132, for use with the system. A seal is provided around neck 134 of tunnel adaptor 132 to prevent cross-contamination of the filtered air with the ambient air.

Sidewall ribs 136 are provided both on the exterior of filter canister 106 and on the interior of filter cylinder 66. Likewise, base ribs 138 are provided on both the bottom of filter canister 106 and on tunnel adaptor 132 where the filter canister rests. The sidewall ribs and the base ribs prevent a seal from forming between filter canister 106 and filter cylinder 66. By preventing the formation of such a seal, the primary filter may be easily removed when it is replaced.

Figure 5:
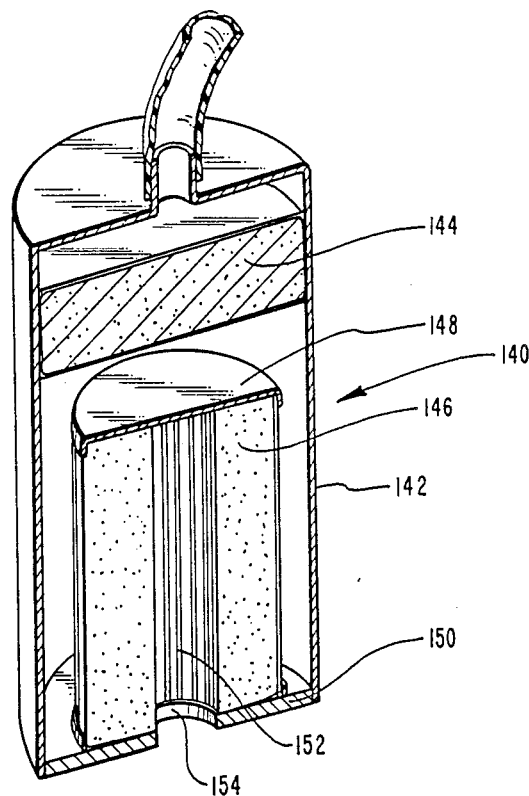
FIG. 5 is a cross-sectional perspective view of yet another embodiment of the filter employed according to the present invention.

An alternate embodiment of a primary filter which may be employed according to the present invention is illustrated in FIG. 5, generally designated at 140. Primary filter 140 includes within filter canister 142 a segment of granular activated charcoal 144, similar to that configuration illustrated in FIG. 3 at 108. A vertically pleated filter 146 is mounted within filter canister 142. A cap 148 provides a seal at the top of vertically pleated filter 146 with a filter base 150 comprised of potting material, such as urethane, providing a seal for the bottom of vertically pleated filter 146. As with primary filter 116 illustrated in FIG. 4, primary filter 140 of FIG. 5 includes a filter exhaust tunnel 152 with a tunnel exhaust port 154 through which the air in the system may exit the primary filter.

Figure 6:
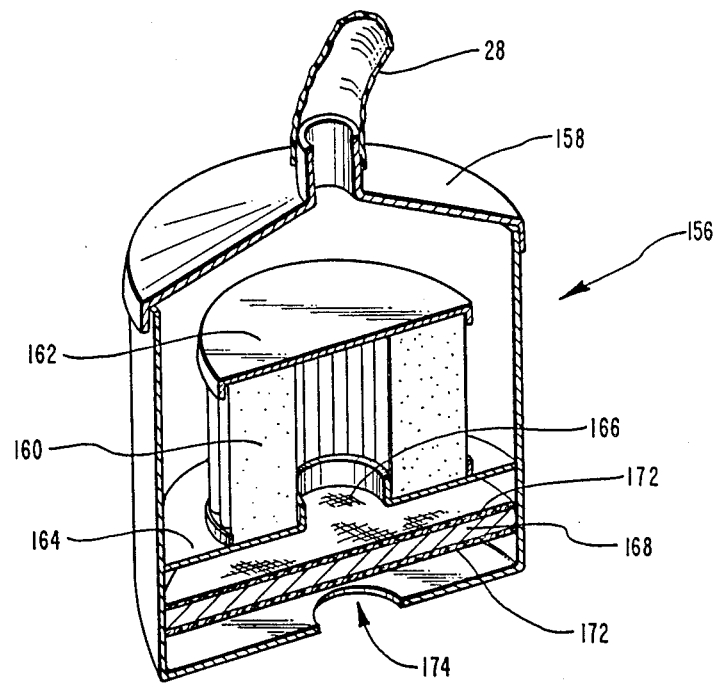
FIG. 6 is a cross-sectional perspective view of one embodiment of a disposable filter which may be used according to the prsent invention.

FIG. 6 illustrates a presently preferred embodiment of a single-use disposable filter for use according to the present invention. In FIG. 6, the disposable filter is generally designated at 156. The laser plume is introduced to filter 156 through inlet tube 28 which is attached to a filter lid 158. After entering filter 156, the plume then passes through a vertically pleated filter 160. Vertically pleated filter 160 includes a filter cap 162 which forces the plume to enter the filter through its sides.

The vertically pleated filter is sealed around its base with a seal 164 so that the laser plume being filtered through the filter all exits the vertically pleated through an exhaust chamber 166 in the center of the base of the vertically pleated filter. Positioned beneath vertically pleated filter 160 within filter 156 is a charcoal filter 168. Charcoal filter 168 includes a center section of ultrafine charcoal 170, coated on each side with a covering 172.

After any particulate matter contained within the laser plume is filtered out by vertically pleated filter 160, any toxic elements within the laser plume are then removed by passing the plume through charcoal filter 168. The filtered air then exits the primary filter through a filter exhaust tunnel 174.

It will be appreciated that the filtering mechanism of the present invention may be embodied in a variety of configurations. For example, the present invention will work effectively using either a single-use, disposable filter or a reuseable filter. Additionally, as can be observed by comparing the filters illustrated in FIGS. 5 and 6, the filter may be configured with the paper filter above or below the charcoal filter without significantly affecting the effectiveness of the primary filter.

When using a disposable filter, such as that illustrated in FIG. 6, for some applications it may be desirable to mount the filter on the side of the housing. The filter could be provided with an inlet tube and an outlet tube attached to the filter and connected to the system.

Figure 7:
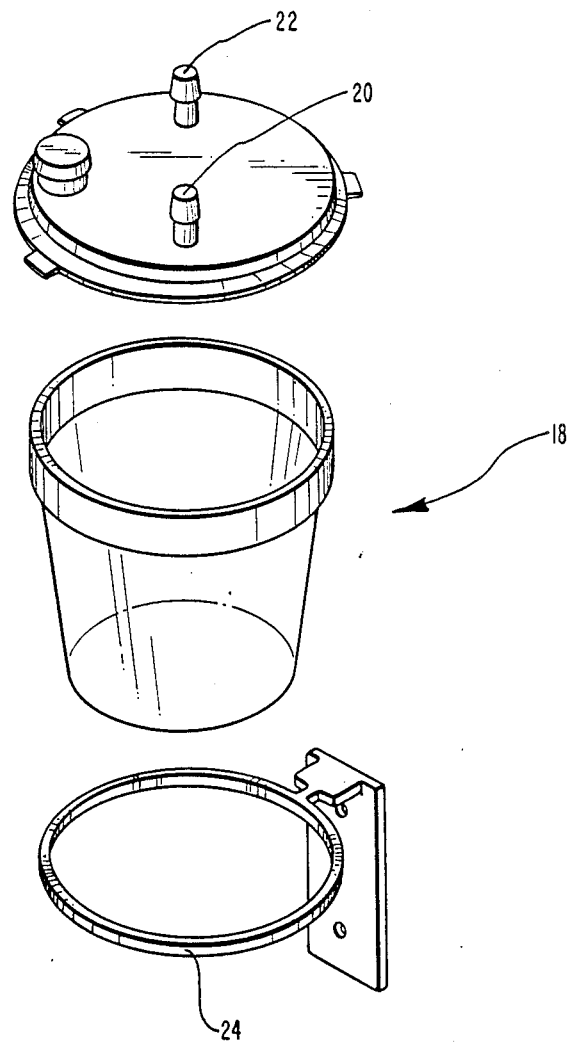
FIG. 7 is an exploded perspective view of the suction canister of the present invention.

FIG. 7 illustrates suction canister 18 in an exploded perspective view. As explained previously, the suction canister is provided with both an inlet port 20 and an outlet port 22 and is utilized in closed surgical procedures for removing a liquid component from the laser plume. Suction canister 18 mounts to a sidewall of the system bottom housing by means of a mounting ring 24. Alternatively, various other mounting methods, as are known in the art, may also be employed to accomplish this purpose. As the laser plume passes through the suction canister, any liquid component within the plume collects within the canister, as the flow of air through the canister is insufficient to carry the heavier liquid particles through outlet port 22.

It will be appreciated that for open surgical procedures the present invention may be operated without using the suction canister 18. The use of the canister for closed procedures extends the life and improves the filtering efficiency of the primary filter by removing the liquid contained within the laser plume.

From the foregoing, it will be appreciated that the present invention provides an efficient and effective system for filtering laser plume from the surgical site.

The filters employed by the present invention are inexpensive, easy to replace, and provide maximum removal efficiency with extended life over filters found in systems of the prior art. The filters may be used in a disposable, non-sterile form or in a reusable form.

The air enhancement system of the present invention is self-contained, thereby eliminating the necessity to rely on hospital vacuum systems and reducing the risk of damaging such systems by introducing to them the particulate debris and other harmful elements unique to laser surgery. Also, due to the unique and advantageous configuration of the system, noise levels are kept to a minimum without reducing the amount of suction available to the system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A self-contained air enhancement system for removing contaminants from a laser plume produced at a surgical site during a medical procedure, said system comprising:

a housing;

an inlet tube for removing the laser plume from the surgical site;

a suction canister secured to said housing and being in communication with said inlet tube for removing liquid components of the contaminants from the laser plume;

a prefilter located in said housing and being in communication with said suction canister for removing particulates from the laser plume;

a filter canister located in said housing and being in communication with said suction canister, said filter canister housing a primary filter capable of removing substantially all of the remaining fine particulates from the laser plume and containing charcoal for removing the odor from the laser plume to produce filtered air;

means located in said housing downstream of said filter canister for creating suction to pull the laser plume in sequence through said inlet tube, said suction canister, said prefilter, and said primary filter;

outlet means in said housing for expelling said filtered air from said housing;

inlet means located in said housing for providing ambient air for cooling said means for creating suction; and means for shielding the laser plume within the housing from cross-contamination of the ambient air for cooling said means for creating suction.

2. A self-contained air enhancement system for removing contaminants from a laser plume during a medical procedure as defined in claim 1, wherein said primary filter is disposable.

3. A self-contained air enhancement system for removing contaminants from a laser plume during a medical procedure as defined in claim 1, wherein said primary filter also includes a vertically pleated filter having a cylindrical shape, said vertically pleated filter providing increased surface area for filtering the laser plume.

4. A self-contained air enhancement system for removing contaminants from a laser plume during a medical procedure as defined in claim 1, comprising a tube reduction means for allowing said inlet tube to be connected to a suction tube having a smaller inner diameter than said inlet tube thereby increasing the suction capabilities of the system.

5. A self-contained air enhancement system for removing contaminants from a laser plume during a medical procedure as defined in claim 1, further comprising a control panel by which the medical personnel may control the amount of suction provided by the system at the surgical site.

6. A self-contained air enhancement system for removing contaminants from a laser plume during a medical procedure as defined in claim 1, wherein said prefilter includes ultrafine charcoal impregnated disks.

7. A self-contained air enhancement system for removing contaminants from a laser plume during a medical procedure as defined in claim 6, wherein said prefilter is disposable.

8. A self-contained air enhancement system for removing contaminants from a laser plume during a medical procedure as defined in claim 7, wherein said prefilter is bonded to said primary filter such that an air-tight bond is created between said prefilter and said primary filter and such that the risk that cross-contamination between the ambient air and the laser plume as the laser plume passes through said prefilter and said primary filter is substantially eliminated.

9. A self-contained air enhancement system for removing contaminants from a laser plume during a medical procedure as defined in claim 1, wherein said prefilter includes a prefilter housing which may be cleansed and is reuseable.

10. A self-contained air enhancement system for removing contaminants from a laser plume during a medical procedure as defined in claim 9, wherein said prefilter is configured such that said prefilter includes ultrafine charcoal impregnated disks.

11. A self-contained air enhancement system for removing contaminants from a laser plume during a medical procedure as defined in claim 1, further comprising indicator means which alerts medical personnel that said primary filter should be replaced.

12. A self-contained air enhancement system for removing contaminants from a laser plume during a medical procedure as defined in claim 11, wherein said indicator means comprises a pressure differential tube and pressure differential switch which measure the difference between the ambient pressure and the pressure generated by said suction means, and a light which is actuated when said pressure differential tube and switch measure a predetermined pressure differential.

13. A self-contained air enhancement system for removing contaminants from a laser plume during a medical procedure as defined in claim 1 wherein said suction canister comprises an inlet and an outlet, said inlet and said outlet being configured respectively to receive tubes having different sized inner diameters.

14. A self-contained air enhancement system for removing contaminants from a laser plume during a medical procedure as defined in claim 13, wherein said inlet means has a smaller diameter than said outlet means thereby increasing the suction capabilities of the system.

15. A self-contained air enhancement system for removing contaminants from a laser plume produced at a surgical site during a medical procedure, said system comprising:
  a housing;
  an inlet tube for removing the laser plume from the surgical site;
  a suction canister secured to said housing and being in communication with said inlet tube for removing liquid components of the contaminants from the laser plume;
  a filter canister located in said housing and being in communication with said suction canister, said filter canister housing a primary filter capable of removing substantially all of the remaining fine particulates from the laser plume and containing charcoal for removing the odor from the laser plume to produce filtered air;
  means located in said housing downstream of said filter canister for creating suction to pull the laser plume in sequence through said inlet tube, said suction canister, said prefilter, and said primary filter;
  outlet means in said housing for expelling said filtered air from said housing;
  inlet means located in said housing for providing ambient air for cooling said means for creating suction; and
  means for shielding the laser plume within the housing from cross-contamination of the ambient air for cooling said means for creating suction.

16. A self-contained air enhancement system for removing contaminants from a laser plume produced at a surgical site during a medical procedure, said system comprising:
  a housing;
  an inlet tube for removing the laser plume from the surgical site;
  a suction canister secured to said housing and being in communication with said inlet tube for removing liquid components of the contaminants from the laser plume;
  a prefilter located in said housing and being in communication with said suction canister for removing particulates from the laser plume;
  a filter canister located said housing and being in communication with said suction canister, said filter canister housing a primary filter capable of removing substantially all of the remaining fine particulates from the laser plume and containing charcoal for removing the odor from the laser plume to produce filtered air;
  means for creating suction located in said housing downstream of said filter canister to pull the laser plume in sequence through said inlet tube, said suction canister, said prefilter, and said primary filter, thereby to preclude contaminants from the laser plume from reaching said means for creating suction;
  an outlet means in said housing for expelling said filtered air from said housing; and
  inlet means located in said housing for providing ambient air for cooling said means for creating suction.

* * * * *

UNITED STATES PATENT AND TRADEMARK OFFICE
CERTIFICATE OF CORRECTION

PATENT NO. : 4,986,839

DATED : January 22, 1991

INVENTOR(S) : THOMAS J. WERTZ et al.

It is certified that error appears in the above-identified patent and that said Letters Patent is hereby corrected as shown below:

```
Column 10, line 2, "air tight" should be --airtight--
Column 13, line 30, "claim 6" should be --claim 1--
Column 14, line 50, after "located" insert --in--
```

Signed and Sealed this

First Day of December, 1992

Attest:

DOUGLAS B. COMER

*Attesting Officer*          *Acting Commissioner of Patents and Trademarks*